(12) United States Patent
Mou et al.

(10) Patent No.: US 11,534,587 B2
(45) Date of Patent: Dec. 27, 2022

(54) BLOOD GLUCOSE MONITORING AND CONTROLLING SYSTEM

(71) Applicant: Microjet Technology Co., Ltd., Hsinchu (TW)

(72) Inventors: Hao-Jan Mou, Hsinchu (TW);
Chi-Feng Huang, Hsinchu (TW);
Yung-Lung Han, Hsinchu (TW);
Wei-Ming Lee, Hsinchu (TW);
Hsuan-Kai Chen, Hsinchu (TW);
Chang-Yen Tsai, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 328 days.

(21) Appl. No.: 16/177,668

(22) Filed: Nov. 1, 2018

(65) Prior Publication Data
US 2019/0151639 A1 May 23, 2019

(30) Foreign Application Priority Data
Nov. 20, 2017 (TW) .................................. 106140074

(51) Int. Cl.
*A61M 37/00* (2006.01)
*G16H 20/17* (2018.01)
(Continued)

(52) U.S. Cl.
CPC ....... *A61M 37/0015* (2013.01); *A61B 5/0004* (2013.01); *A61B 5/14532* (2013.01);
(Continued)

(58) Field of Classification Search
CPC ...... A61M 37/0015; A61M 2037/0023; A61M 2037/0046; A61M 2230/201; G16H 20/17;
(Continued)

(56) References Cited

U.S. PATENT DOCUMENTS

| 6,558,361 B1 | 5/2003 | Yeshurun |
| 6,908,453 B2 | 6/2005 | Fleming et al. |

(Continued)

FOREIGN PATENT DOCUMENTS

| CN | 101125086 A | 2/2008 |
| CN | 205626630 U | 10/2016 |

(Continued)

OTHER PUBLICATIONS

Kim, Hanseup, "An Integrated Electrostatic Peristaltic 18-Stage Gas Micropump With Active Microvalves", Journal of Microelectromechanical Systems, vol. 24, No. 1, Feb. 2015 (Year: 2015) (Year: 2015).*

(Continued)

*Primary Examiner* — Sean P Dougherty
*Assistant Examiner* — Alexander H Connor
(74) *Attorney, Agent, or Firm* — Birch, Stewart, Kolasch & Birch, LLP

(57) ABSTRACT

A blood glucose monitoring and controlling system includes a detecting device and a liquid supplying device. The detecting device includes a first microneedle patch, a liquid pumping actuator, a sensor and a monitoring and controlling chip. The liquid supplying device includes a second microneedle patch, a liquid supplying actuator, a liquid supplying chamber and a liquid supplying and controlling chip. The detecting device is used to measure the blood glucose level of the user, and the liquid supplying device is used to supply insulin liquid. While the detecting device measures that the blood glucose level of the user is abnormal, the liquid supplying device is actuated to inject the insulin liquid into the user's body, thereby stabilizing the user's blood glucose level constantly.

15 Claims, 11 Drawing Sheets

(51) Int. Cl.
*A61B 5/00* (2006.01)
*A61B 5/145* (2006.01)
*A61B 5/15* (2006.01)
*A61B 5/157* (2006.01)

(52) U.S. Cl.
CPC ........ A61B 5/157 (2013.01); A61B 5/150221 (2013.01); A61B 5/150984 (2013.01); G16H 20/17 (2018.01); *A61M 2037/0023* (2013.01); *A61M 2037/0046* (2013.01); *A61M 2230/201* (2013.01)

(58) Field of Classification Search
CPC .............. A61B 5/0004; A61B 5/14532; A61B 5/150221; A61B 5/150984; A61B 5/157
See application file for complete search history.

(56) References Cited

U.S. PATENT DOCUMENTS

| | | | | |
|---|---|---|---|---|
| 7,008,193 | B2* | 3/2006 | Najafi | F04B 45/047 417/313 |
| 8,105,057 | B2* | 1/2012 | Chen | F04B 43/046 417/413.1 |
| 8,579,606 | B2* | 11/2013 | Chen | F04B 43/043 137/856 |
| 2003/0187423 | A1 | 10/2003 | Wilkinson et al. | |
| 2003/0231967 | A1 | 12/2003 | Najafi et al. | |
| 2004/0019331 | A1* | 1/2004 | Yeshurun | A61B 5/150282 604/173 |
| 2008/0035875 | A1 | 2/2008 | Tai et al. | |
| 2008/0051711 | A1 | 2/2008 | Mounce et al. | |
| 2009/0259176 | A1* | 10/2009 | Yairi | A61M 35/10 604/290 |
| 2010/0262117 | A1* | 10/2010 | Magni | G16H 20/17 604/504 |
| 2011/0105952 | A1* | 5/2011 | Bernstein | A61B 5/150412 600/573 |
| 2013/0225956 | A1* | 8/2013 | Huang | A61B 5/685 600/345 |
| 2014/0364764 | A1* | 12/2014 | Jung | A61B 5/15113 600/579 |
| 2015/0202418 | A1* | 7/2015 | Simon | A61B 5/150755 604/319 |
| 2016/0095541 | A1 | 4/2016 | Wang et al. | |
| 2016/0296149 | A1 | 10/2016 | Polsky et al. | |
| 2017/0000391 | A1 | 1/2017 | Wasson et al. | |
| 2018/0321187 | A1* | 11/2018 | Gu | G01N 27/416 |

FOREIGN PATENT DOCUMENTS

| | | |
|---|---|---|
| CN | 106390277 A | 2/2017 |
| JP | 2010-507431 A | 3/2010 |
| TW | 201335483 A1 | 9/2013 |
| TW | M537174 U | 2/2017 |

OTHER PUBLICATIONS

Kim, Hanseup, "An Integrated Electrostatic Peristaltic 18-Stage Gas Micropump With Active Microvalves", Journal of Microelectromechanical Systems, vol. 24, No. 1, Feb. 2015 (Year: 2015).*
Katz, Evgeny, "Magneto-switchable Electrodes and Electrochemical Systems", Electroanalysis 2016, 28, 904-919 (Year: 2016).*
Bogdanksi, Jack: "System in Package: Better performance, smaller footprint" Embedded Computing. Published Feb. 1, 2009 accessed @https://www.embeddedcomputing.com/technology/processing/chips-and-socs/system-in-package-better-performance-smaller-footprint Mar. 3, 2022 (Year: 2009).*
"Opposite." Merriam-Webster.com Dictionary, Merriam-Webster, https://www.merriam-webster.com/dictionary/opposite. Accessed Mar. 3. 202 with waybackmachine. archived Mar. 26, 2016 (Year: 2016).*
Extended European Search Report dated Apr. 23, 2019 for Application No. 18203738.2.

* cited by examiner

BLOOD GLUCOSE MONITORING AND CONTROLLING SYSTEM

FIELD OF THE INVENTION

The present disclosure relates to a blood glucose monitoring and controlling system, and more particularly to a blood glucose monitoring and controlling system capable of monitoring and controlling blood glucose level of human subject for long period of time.

BACKGROUND OF THE INVENTION

For diabetes mellitus patients, self-detection of blood glucose plays an important role in the management of blood glucose. Currently, the blood glucose meter used to measure the blood glucose is inconvenient to carry, so it is difficult for patients to monitor the blood glucose level when they go out. In addition, in the process of measuring the blood glucose, sometimes there is no bleeding or too little blood is drawn when a needle is employed to draw the blood. Hence, it is necessary to use the needle again or force to squeeze the blood out. This may cause the psychological fear of the patient, and forcing to squeeze the blood out may result in incorrect measuring results. Moreover, when the patient is aware of abnormal blood glucose level, it is unlikely to bring the blood glucose level back to the normal state in a short time by just taking oral medicine or an injection immediately. Accordingly, it is difficult to stabilize the blood glucose level constantly and may lead to complications that damage the patient's body.

Therefore, there is a need of providing a blood glucose monitoring and controlling system to address the above-mentioned issues. The blood glucose monitoring and controlling system should be intelligent, safe, portable and painless, and allow the patients to measure the blood glucose level in daily life easily and at anytime so as to stabilize the blood glucose level for a long period of time and address the issues that the patient fails to stabilize the blood glucose level.

SUMMARY OF THE INVENTION

The conventional insulin injection method causes the patients' pain and the blood glucose meter is inconvenient to carry. The object of the present disclosure is to provide a blood glucose monitoring and controlling system to overcome the problems in the current situation. In accordance with an aspect of the present disclosure, a blood glucose monitoring and controlling system is provided. The blood glucose monitoring and controlling system includes a detecting device and a liquid supplying device. The detecting device includes a first microneedle patch, a liquid pumping actuator, a sensor and a monitoring and controlling chip. The first microneedle patch includes a plurality of hollow microneedles to be attached to and punctured into skin of a human subject to draw tissue liquid. The liquid pumping actuator includes a liquid guiding channel and a first actuating unit. The liquid guiding channel is in fluid communication with the first microneedle patch. The first actuating unit is actuated to generate a pressure difference in the liquid guiding channel to draw the tissue liquid and allow the liquid guiding channel to draw the tissue liquid transported by the hollow microneedles. The sensor is disposed in communication with the liquid guiding channel to measure a blood glucose level in the tissue liquid and transmits the measured data of the blood glucose level to the monitoring and controlling chip. The monitoring and controlling chip generates blood glucose level information by calculating the measured data and transmits a notification of the blood glucose level information. The liquid supplying device includes a second microneedle patch, a liquid supplying actuator, a liquid supplying chamber and a liquid supplying and controlling chip. The second microneedle patch includes a plurality of hollow microneedles to be attached to and punctured into the skin of the human subject. The liquid supplying actuator includes a liquid injection channel and a second actuating unit. The liquid injection channel is in fluid communication with the second microneedle patch and the liquid supplying chamber. The liquid supplying chamber stores insulin liquid and the second actuating unit is actuated to compress the liquid injection channel to conduct liquid transportation. The liquid supplying and controlling chip receives the notification of the blood glucose level information transmitted from the monitoring and controlling chip of the detecting device so as to actuate the second actuating unit of the liquid supplying device so that a pressure difference is generated in the liquid injection channel to transport the insulin liquid stored in the liquid supplying chamber and guide the insulin liquid to the hollow microneedles, thereby injecting the insulin liquid into subcutaneous tissue of the human subject to stabilize the blood glucose level.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
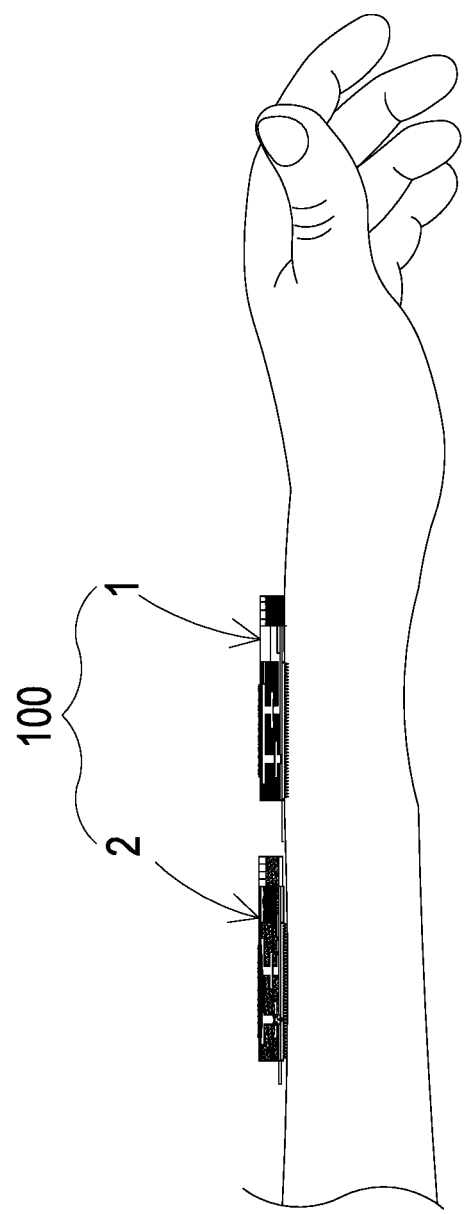
FIG. 1 is a schematic structural view illustrating a blood glucose monitoring and controlling system in use according to an embodiment of the present disclosure.
Figure 2:
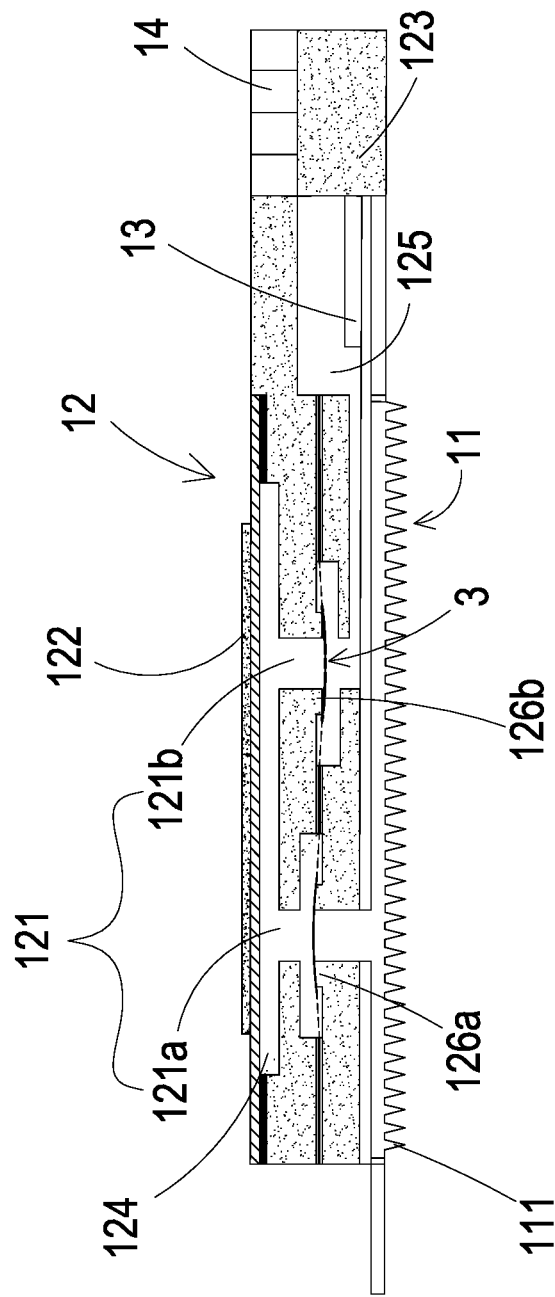
FIG. 2 is a cross sectional view illustrating a detecting device of the blood glucose monitoring and controlling system of FIG. 1.
Figure 3:
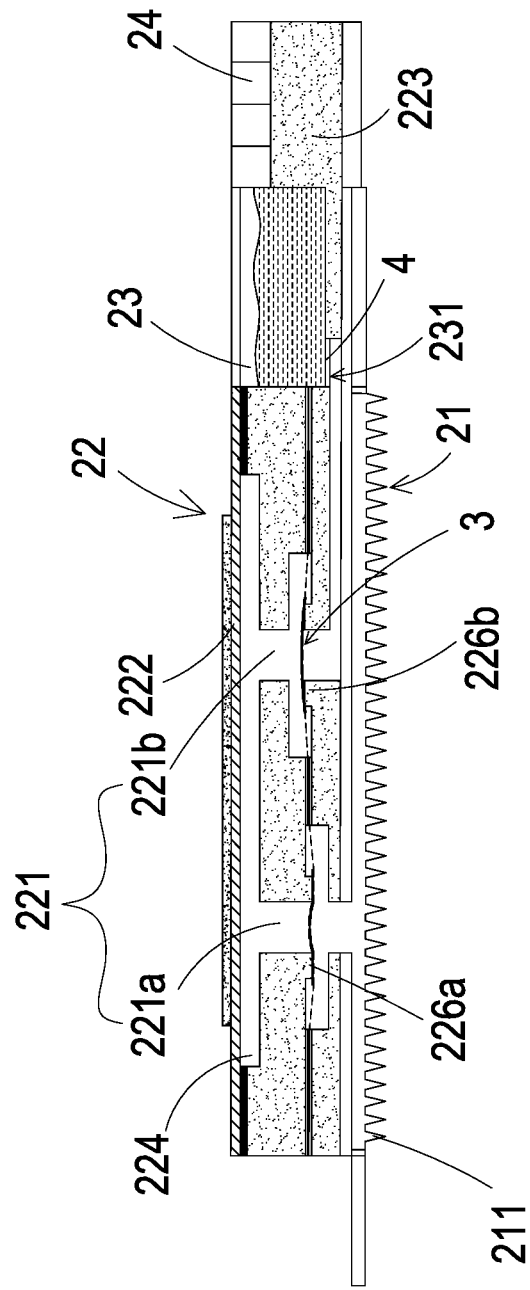
FIG. 3 is a cross sectional view illustrating a liquid supplying device of the blood glucose monitoring and controlling system of FIG. 1.

Please refer FIGS. 1, 2 and 3. The present discourse provides a blood glucose monitoring and controlling system 100 including at least one detecting device 1, at least one first microneedle patch 11, at least one liquid pumping actuator 12, at least one sensor 13, at least one monitoring and controlling chip 14, a plurality of hollow microneedles, at least one tissue liquid, at least one liquid guiding channel 121, at least one first actuating unit 122, at least one blood glucose level information, at least one liquid supplying device 2, at least one second microneedle patch 21, at least one liquid supplying actuator 22, at least one liquid supplying chamber 23, at least one liquid supplying and controlling chip 24, at least one liquid injection channel 221, at least one second actuating unit 222 and at least one insulin liquid. The number of the detecting device 1, the first microneedle patch 11, the liquid pumping actuator 12, the sensor 13, the monitoring and controlling chip 14, the tissue liquid, the liquid guiding channel 121, the first actuating unit 122, the blood glucose level information, the liquid supplying device 2, the second microneedle patch 21, the liquid supplying actuator 22, the liquid supplying chamber 23, the liquid supplying and controlling chip 24, the liquid injection channel 221, the second actuating unit 222 and the insulin liquid is exemplified by one for each in the following embodiments but not limited thereto. It is noted that the detecting device 1, the first microneedle patch 11, the liquid-pumping actuator 12, the sensor 13, the monitoring and controlling chip 14, the tissue liquid, the liquid guiding channel 121, the first actuating unit 122, the blood glucose level information, the liquid supplying device 2, the second microneedle patch 21, the liquid supplying actuator 22, the liquid supplying chamber 23, the liquid supplying and controlling chip 24, the liquid injection channel 221, the second actuating unit 222 and the insulin liquid can also be provided in plural numbers.

Please refer to FIGS. 1 to 3, a blood glucose monitoring and controlling system 100 is provided. As shown in FIG. 1, the blood glucose monitoring and controlling system 100 includes a detecting device 1 and a liquid supplying device 2. As shown in FIG. 2, the detecting device 1 includes a first microneedle patch 11, a liquid pumping actuator 12, a sensor 13 and a monitoring and controlling chip 14. As shown in FIG. 3, the liquid supplying device 2 includes a second microneedle patch 21, a liquid supplying actuator 22, a liquid supplying chamber 23 and a liquid supplying and controlling chip 24. In this embodiment, the detecting device 1 is used to measure the blood glucose level of the user (e.g., the human subject), and the liquid supplying device 2 is used to supply insulin liquid. While the detecting device 1 detects that the blood glucose level of the user is abnormal, the liquid supplying device 2 is actuated to inject the insulin liquid into the user's body so as to achieve the purposes of monitoring and controlling the blood glucose.

Please refer to FIGS. 1 and 2. In this embodiment, the liquid pumping actuator 12 of the detecting device 1 includes a liquid guiding channel 121, a first actuating unit 122, a first carrier body 123, a first compressing chamber 124 and a liquid storage chamber 125. The first compressing chamber 124, the liquid storage chamber 125 and the liquid guiding channel 121 are concavely formed in the first carrier body 123 respectively. The liquid guiding channel 121 further includes an inlet channel 121a and a liquid storage channel 121b, which are separately disposed in the first carrier body 123. The inlet channel 121a and the liquid storage channel 121b are in fluid communication with each other through the first compressing chamber 124, and the liquid storage channel 121b is in fluid communication with the liquid storage chamber 125. The sensor 13 is disposed in the liquid storage chamber 125 for sensing the liquid stored in the liquid storage chamber 125. The first actuating unit 122 is constructed on the first carrier body 123 and covers and seals the first compressing chamber 124. When the first actuating unit 122 is actuated, a suction force is generated to draw the fluid. The first microneedle patch 11 is attached on the first carrier body 123 and is in fluid communication with the inlet channel 121a. The first microneedle patch 11 has plural hollow microneedles 111. The plural hollow microneedles 111 may be punctured into skin of a human subject with minimal invasion. In some embodiments, the plural hollow microneedles 111 may be punctured into the skin of the human subject in combination with noninvasive methods. The sensor 13 and the monitoring and controlling chip 14 are integrated on the first carrier body 123 via microelectromechanical systems (MEMS) procedure. The sensor 13 is packaged in a system-in-package manner on the first carrier body 123. The monitoring and controlling chip 14 is packaged in a system-in-package manner on the first carrier body 123 for controlling the actuation of the liquid pumping actuator 12 and receiving and analyzing the measured data from the sensor 13. The first actuating unit 122 of the liquid pumping actuator 12 covers and seals the first compressing chamber 124. The first actuating unit 122 is driven to vibrate up and down to change the volume of the first compressing chamber 124 so that the pressure in the first compressing chamber 124 changes and a suction force is generated accordingly.

Figure 8:
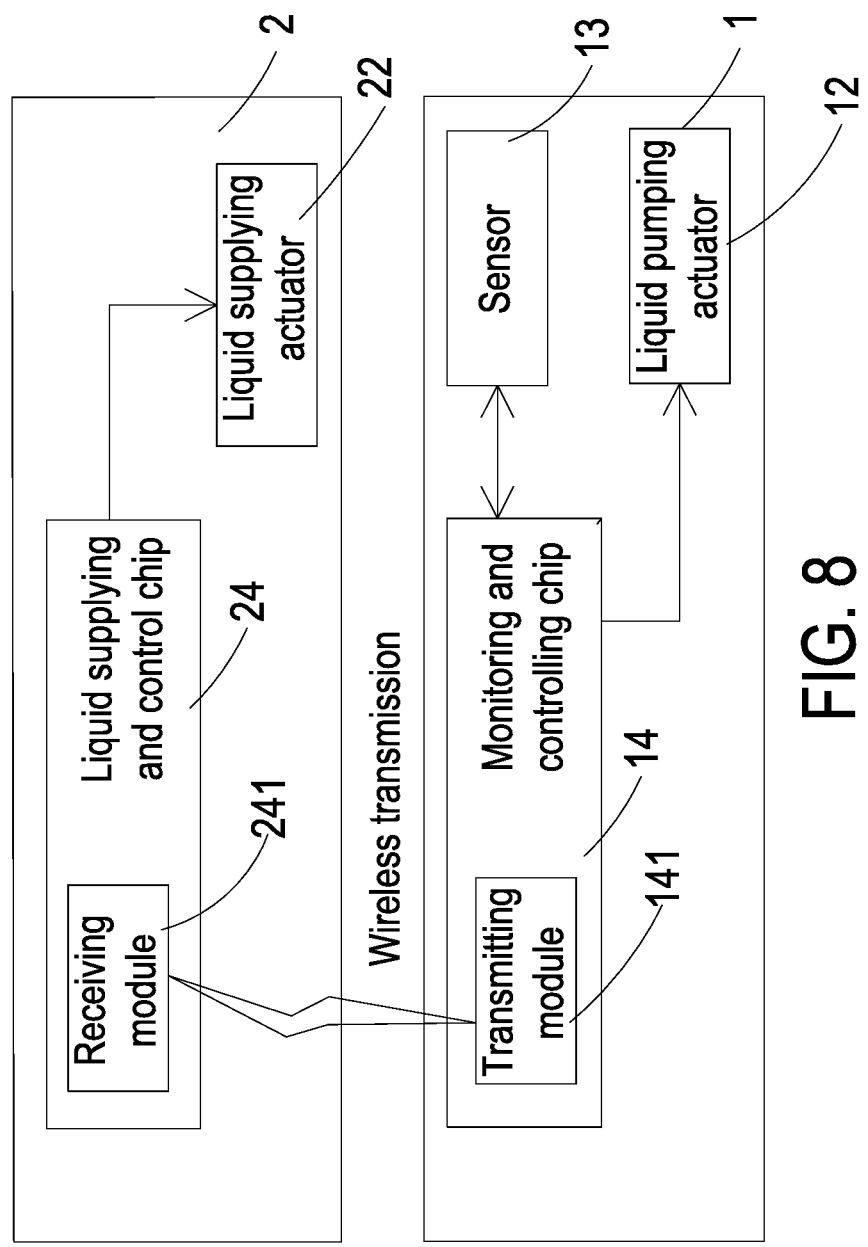
FIG. 8 is a block diagram of the blood glucose monitoring and controlling system of FIG. 1.

Please refer to FIGS. 1 and 8. In this embodiment, when the plural hollow microneedles 111 of the first microneedle patch 11 are punctured into the human subject, the monitoring and controlling chip 14 drives the first actuating unit 122 of the liquid pumping actuator 12 to vibrate vertically to expand or compress the volume of the first compressing chamber 124, so that the pressure in the first compressing chamber 124 changes and the suction force is generated accordingly. The suction force is generated in the inlet channel 121a and makes the plural hollow microneedles 111 of the first microneedle patch 11 draw the tissue liquid from the human subject. The tissue liquid of the human subject flows through the first compressing chamber 124 and the liquid storage channel 121b into the liquid storage chamber 125. Meanwhile, the sensor 13 disposed in the liquid storage chamber 125 measures the blood glucose level in the tissue liquid to generate a measured data and then transmits the measured data to the monitoring and controlling chip 14. The monitoring and controlling chip 14 generates a blood glucose level information by calculating the measured data. In addition, the monitoring and controlling chip 14 includes a transmitting module 141 (as shown in FIG. 8) for transmitting a notification of the blood glucose level information. In this embodiment, the tissue liquid is a human subcutaneous tissue liquid. The liquid supplying and controlling chip 24 of the liquid supplying device 2 also includes a receiving module 241 (as shown in FIG. 8) for receiving the notification of the blood glucose level information transmitted from the monitoring and controlling chip 14 of the detecting device 1, so that the liquid supplying and controlling chip 24 drives the actuation of the liquid supplying actuator 22 rapidly to transport and inject the insulin liquid stored in the liquid supplying chamber 23 into the user's body for stabilizing the blood glucose level of the user.

Please refer to FIGS. 1 and 3. In this embodiment, the liquid supplying actuator 22 of the liquid supplying device 2 includes a liquid injection channel 221, a second actuating unit 222, a second carrier body 223 and a second compressing chamber 224. The second compressing chamber 224 and the liquid injection channel 221 are concavely formed in the second carrier body 223. The injection channel 221 further includes an outlet channel 221a and a liquid guiding channel 221b, which are separately disposed in the second carrier body 223. The outlet channel 221a and the liquid guiding channel 221b are in fluid communication with each other through the second compressing chamber 224, and the liquid guiding channel 221b is in fluid communication with the liquid supplying chamber 23. The liquid supplying chamber 23 stores the insulin liquid therein and has a liquid supplying outlet 231. A switch valve 4 is disposed in the liquid supplying outlet 231 for controlling the efflux of the insulin liquid. The second microneedle patch 21 is attached on the second carrier body 223 and is in fluid communication with outlet channel 221a. The second microneedle patch 21 includes plural hollow microneedles 211. The plural hollow microneedles 211 may be punctured into the skin of the human subject with minimal invasion so as to inject the insulin liquid. In some embodiments, the plural hollow microneedles 211 may be punctured into the skin of the human subject in combination with noninvasive methods so as to inject the insulin liquid. The liquid supplying and controlling chip 24 is integrated on the second carrier body 223 via microelectronmechanical systems (MEMS) procedure and configured to control the actuation of the liquid supplying actuator 22. In addition, the liquid supplying and controlling chip 24 includes a receiving module 241 (as shown in FIG. 8) for receiving the blood glucose level information transmitted from the transmitting module 141 of the monitoring and controlling chip 14 of the detecting device 1. The second actuating unit 222 of the liquid supplying actuator 22 covers and seals the second compressing chamber 224. The second actuating unit 222 is actuated to vibrate up and down to change the volume of the second compressing chamber 224, so that the pressure in the second compressing chamber 224 changes to form a pressure difference, by which a discharging force is generated accordingly for guiding and discharging the insulin liquid.

Please refer to FIGS. 1 and 3. In this embodiment, when the plural hollow microneedles 211 of the second microneedle patch 21 are punctured into the human subject, the liquid supplying and controlling chip 24 drives the second actuating unit 222 of the liquid supplying actuator 22 to vibrate vertically to expand or compress the volume of the second compressing chamber 224, so that the pressure in the second compressing chamber 124 changes to form the pressure difference that generates the discharging force. The discharging force causes the insulin liquid in the liquid supplying chamber 23 to flow through the second compressing chamber 224 and the liquid injection channel 221 into the second microneedle patch 21 so as to inject the insulin liquid into the user's body via the hollow microneedles 211 of the second microneedle patch 21.

In this embodiment, the plural hollow microneedles 111 of the first microneedle patch 11 or the plural hollow microneedles 211 of the second microneedle patch 21 are micron-sized needles capable of puncturing into the skin. The hollow microneedles 111, 211 may be made of high molecular polymer, metal or silicon. Preferably but not exclusively, the hollow microneedles 111, 211 are made of silicon dioxide with high biocompatibility. The size of the hollow part inside each hollow microneedle 111, 211 may be suitable for allowing the insulin molecules to pass through. Preferably, the hollow microneedle 111, 211 has an internal diameter ranging from 10 μm to 550 μm. The hollow microneedle 111, 211 has a length ranging from 400 μm to 900 μm. The hollow microneedles 111, 211 can puncture into human's subcutaneous tissue to reach a depth and without contacting any nerve so that the puncture of the hollow microneedles 111, 211 is painless. The hollow microneedles 111 are disposed on the first microneedle patch 11 and arranged in an array, and the hollow microneedles 211 are disposed on the second microneedle patch 21 and arranged in an array. The hollow microneedles 111 are spaced from each other a distance greater than 200 μm, and so are the hollow microneedles 211. In other words, any two adjacent hollow microneedles 111, 211 are spaced from each other the distance greater than 200 μm, by which the hollow microneedles 111 would not interfere with each other regarding the liquid transportation and so does the hollow microneedles 211. When blockage of one or more hollow microneedles 111, 211 occurs, the rest of the hollow microneedles 111, 211 without blockage can still function. That is, the arrangement of the hollow microneedles 111, 211 in the array can prevent the entire liquid flowing function from being impacted. In other words, the hollow microneedles 111, 211 maintain such injecting/drawing function as a whole.

Figure 4:
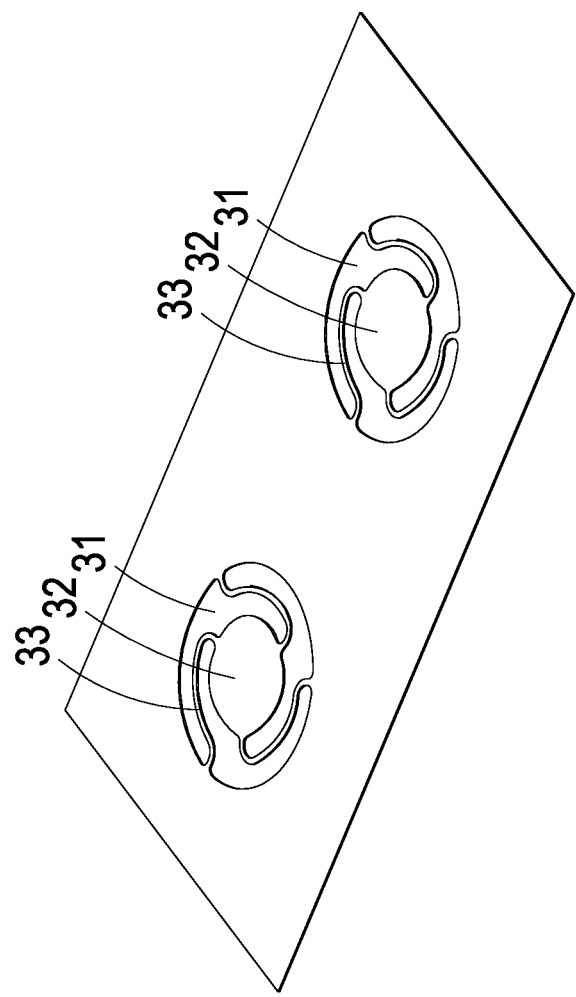
FIG. 4 is a schematic structural view illustrating a valve membrane of the blood glucose monitoring and controlling system of FIG. 1.

Please refer to FIGS. 2 and 4. In the detecting device 1 of the blood glucose monitoring and controlling system 100, a valve membrane 3 is disposed in both of the inlet channel 121a and the liquid storage channel 121b, and a plurality of through holes 31 are formed on the valve membrane 3. There are first convex structures 126a, 126b respectively formed in the inlet channel 121a and the liquid storage channel 121b of the first carrier body 123, wherein the protruding direction of the first convex structure 126a of the inlet channel 121a is opposite to the protruding direction of the first convex structure 126b of the liquid storage channel 121b. In this embodiment, the protruding direction of the first convex structure 126a of the inlet channel 121a is upward, but on the contrary, the protruding direction of the first convex structure 126b of the inlet channel 121b is downward. The valve membrane 3 has plural through holes 31 spatially corresponding to the partial area of the inlet channel 121a and the liquid storage channel 121b and has a central part 32 connected to plural connection parts 33. The central part 32 can be elastically supported by the connection parts 33 that divide the space between the central part 32 and the connection parts 33 into the through holes 31. In this way, the first convex structure 126a of the inlet channel 121a and the first convex structure 126b of the liquid storage channel 121b abut against the valve membrane 3 so as to seal the plural through holes 31, respectively, and a pre-force is formed. The pre-force brings the valve membrane 3 into close contact with the first convex structures 126a, 126b. In the above-mentioned configuration, when the first actuating unit 122 is non-enabled, the central parts 32 of the valve membrane 3 in the inlet channel 121a and the liquid storage channel 121b can close the inlet channel 121a and the liquid storage channel 121b, respectively. Therefore, the tissue liquid transported between the inlet channel 121a and the liquid storage channel 121b will not be reversely returned. That is, the tissue liquid flows in a single direction from the inlet channel 121a to the liquid storage channel 121b without flowing back.

Please refer to FIGS. 3 and 4. In the liquid supplying device 2 of the blood glucose monitoring and controlling system 100, a valve membrane 3 is disposed in both of the outlet channel 221a and the liquid guiding channel 221b, and a plurality of through holes 31 are formed on the valve membrane 3. There are second convex structures 226a, 226b respectively formed in the outlet channel 221a and the liquid guiding channel 221b of the second carrier body 223, wherein the protruding direction of the second convex structure 226a of the outlet channel 221a is opposite to the protruding direction of the second convex structure 226b of the liquid guiding channel 221b. In this embodiment, the protruding direction of the second convex structure 226a of the outlet channel 221a is downward, but on the contrary, the protruding direction of the second convex structure 226b of the liquid guiding channel 221b is upward. The valve membrane 3 has plural through holes 31 spatially corresponding to the partial area of the outlet channel 221a and the liquid guiding channel 221b and has a central part 32 connected to plural connection parts 33. The through holes 31 are disposed between the connection parts 33. The central part 32 can be elastically supported by the connection parts 33 that divide the space between the central part 32 and the connection parts 33 into the through holes 31. In this way, the second convex structure 226a of the outlet channel 221a and the second convex structure 226b of the liquid guiding channel 221b abut against the valve membrane 3 so as to seal the plural through holes 31, respectively, and a pre-force is formed. The pre-force brings the valve membrane 3 into close contact with the second convex structures 226a, 226b. In the above-mentioned configuration, when the second actuating unit 222 is non-enabled, the central parts 32 of the valve membrane 3 in the outlet channel 221a and the liquid guiding channel 221b can close the outlet channel 221a and the liquid guiding channel 221b, respectively. Therefore, the tissue liquid transported between the outlet channel 221a and the liquid guiding channel 221b will not be reversely returned. That is, the tissue liquid flows in a single direction from the liquid guiding channel 221b to the outlet channel 221a without flowing back.

Figure 5A:
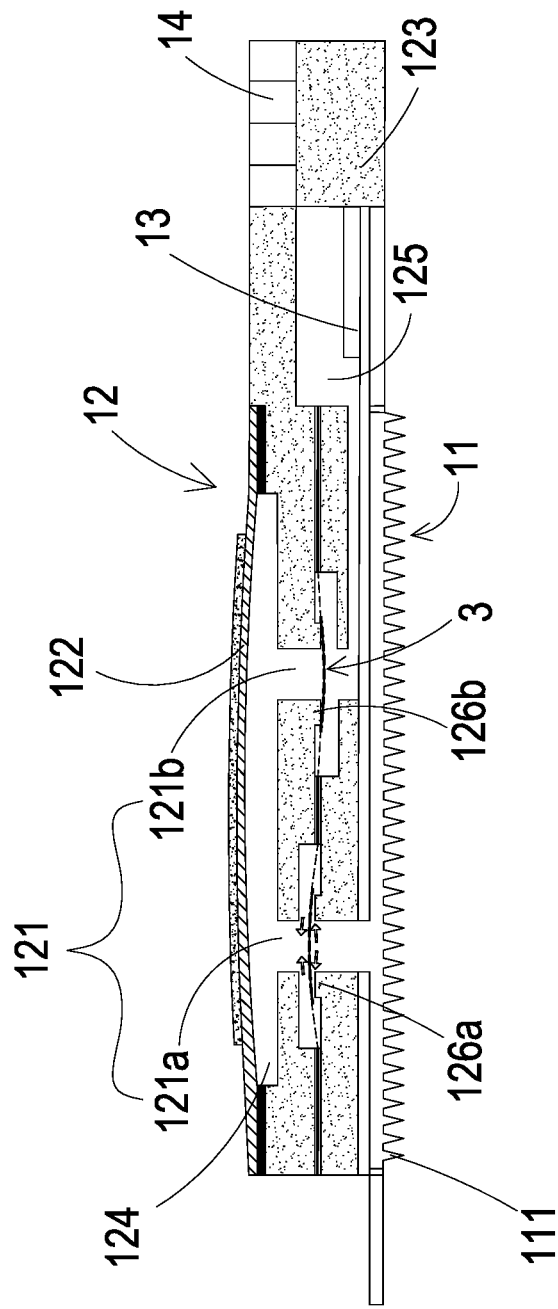
FIGS. 5A and 5B show the actuations of the detecting device of the blood glucose monitoring and controlling system of FIG. 2.
Figure 5B:
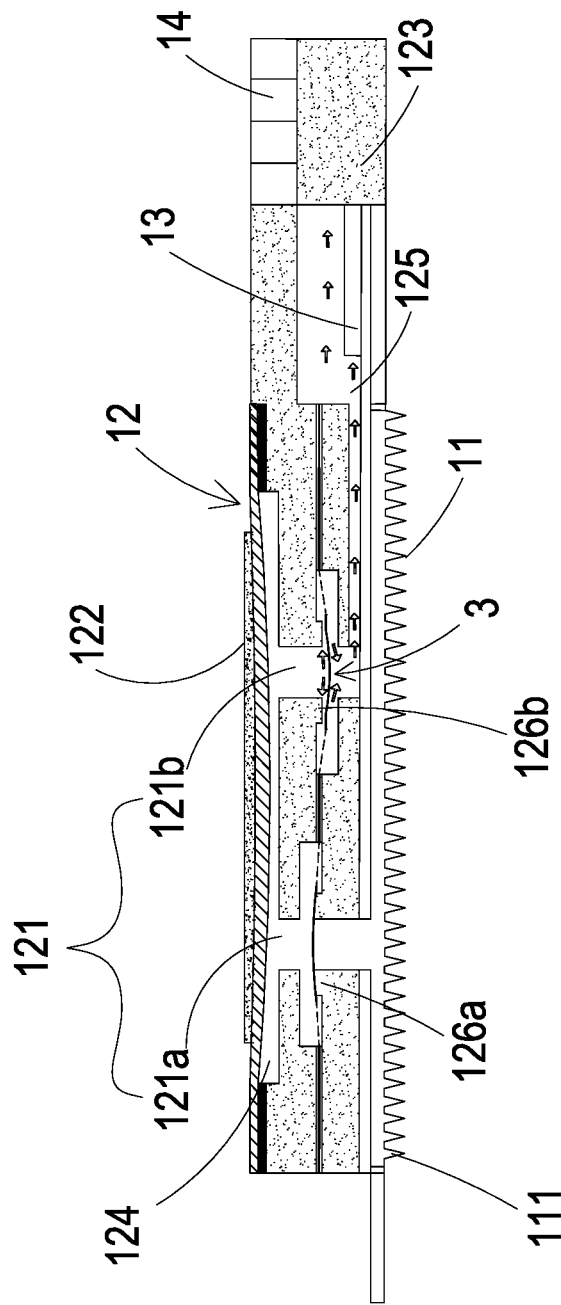

Please refer to FIGS. 5A and 5B. When the liquid pumping actuator 12 of the detecting device 1 is actuated under control of the monitoring and controlling chip 14, the first actuating unit 122 is driven to deform and vibrate up and down. As shown in FIG. 5A, when the first actuating unit 122 moves upwardly, the volume of the first compressing chamber 124 is enlarged and a negative pressure is generated to drive the valve membrane 3 in the inlet channel 121a to move upwardly, so that the through hole 31 of the valve membrane 3 (as show in FIG. 4) is separated from the first convex structure 126a. Meanwhile, the inlet channel 121a is in fluid communication with the first compressing chamber 124. Since the volume of the first compressing chamber 124 is enlarged to generate the pressure difference, the suction force is generated in the inlet channel 121a. In this way, the suction force is also generated in the first microneedle patch 11 in fluid communication with the inlet channel 121a to draw the tissue liquid into the first microneedle patch 11 and allow the tissue liquid to flow through the inlet channel 121a into the first compressing chamber 124. As shown in FIG. 5B, since the monitoring and controlling chip 14 continuously issues the driving signal to the liquid pumping actuator 12, the first actuating unit 122 moves downwardly. Meanwhile, the volume of the first compressing chamber 124 is compressed to generate the pressure difference, and a positive pressure is generated to drive the valve membrane 3 in liquid storage channel 121b to move downwardly, so that the through hole 31 of the valve membrane 3 is separated from the first convex structure 126b. The tissue liquid within the first compressing chamber 124 is pushed into the liquid storage channel 121b in response to the positive pressure, and then is transported to the liquid storage chamber 125. In this way, the sensor 3 measures the blood glucose level in the tissue liquid and generates measured data correspondingly.

Then, the sensor 3 transmits the measured data to the monitoring and controlling chip 14 for calculation. The monitoring and controlling chip 14 generates the blood glucose level information by calculating the measured data. In case that the blood glucose level information indicates that the blood glucose level is abnormal and the insulin liquid needs to be supplied to the user, the transmitting module 141 of the monitoring and controlling chip 14 of the detecting device 1 issues the notification of the blood glucose level information to the liquid supplying device 2 so as to actuate the liquid supplying device 2 to perform an injection operation for supplying the insulin liquid to the user.

Figure 6A:
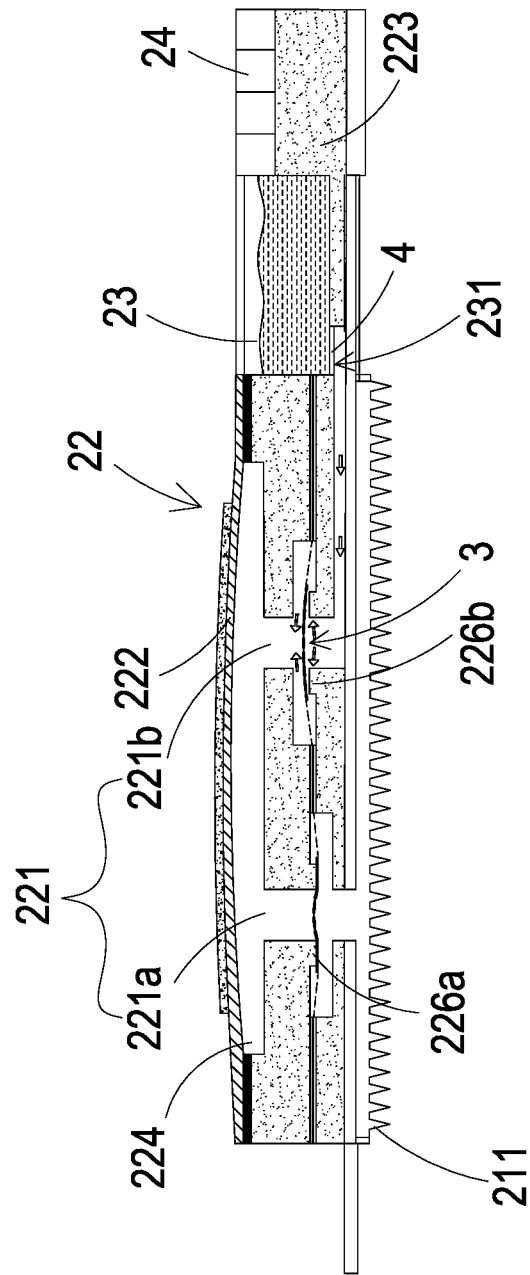
FIGS. 6A and 6B show the actuations of the liquid supplying device of the blood glucose monitoring and controlling system of FIG. 3.
Figure 6B:
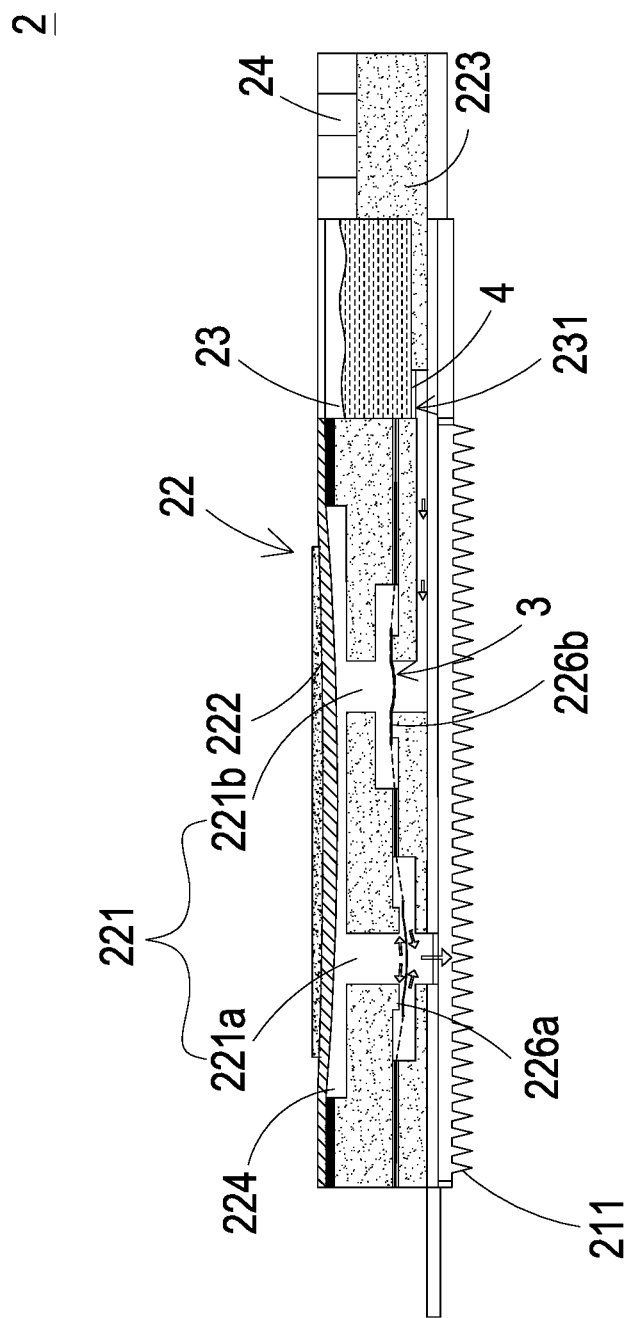

Please refer to FIGS. 6A, 6B and 8. When the liquid supplying device 2 receives the notification of blood glucose level information transmitted from the monitoring and controlling chip 14 of the detecting device 1, the liquid supplying actuator 22 is actuated rapidly by the liquid supplying and controlling device 24, so that the second actuating unit 222 is driven to deform and vibrate up and down. As shown in FIG. 6A, when the second actuating unit 222 moves upwardly, the volume of the second compressing chamber 224 is enlarged to generate the pressure difference and a negative pressure is generated to drive the valve membrane 3 in the liquid guiding channel 221b to move upwardly, so that the through hole 31 of the valve membrane 3 (as show in FIG. 4) is separated from the second convex structure 226a. Meanwhile, the liquid guiding channel 221b is in fluid communication with the second compressing chamber 224. Since the volume of the second compressing chamber 224 is enlarged to generate the pressure difference, the suction force is generated in the liquid guiding channel 221b and the switch valve 4 in the liquid supplying outlet 231 is in the open state under control of the liquid supplying and controlling chip 24. In this way, the insulin liquid in the liquid supplying chamber 23 in fluid communication with the liquid guiding channel 221b is inhaled, and it makes the insulin liquid flow through the liquid guiding channel 221b into the second compressing chamber 224. As shown in FIG. 6B, since the liquid supplying and controlling chip 24 continuously issues the driving signal to the liquid supplying actuator 22, the second actuating unit 222 moves downwardly. Meanwhile, the volume of the second compressing chamber 224 is compressed to generate the pressure difference, and a positive pressure is generated to drive the valve membrane 3 in the outlet channel 221a to move downwardly, so that the through hole 31 of the valve membrane 3 (as shown in FIG. 4) is separated from the second convex structure 226b. The insulin liquid within the second compressing chamber 224 is pushed into the liquid guiding channel 221a in response to the positive pressure, and then injected into the user's body through the hollow microneedles 211 of the second microneedle patch 21 so as to stabilize the blood glucose level of the user.

Figure 7A:
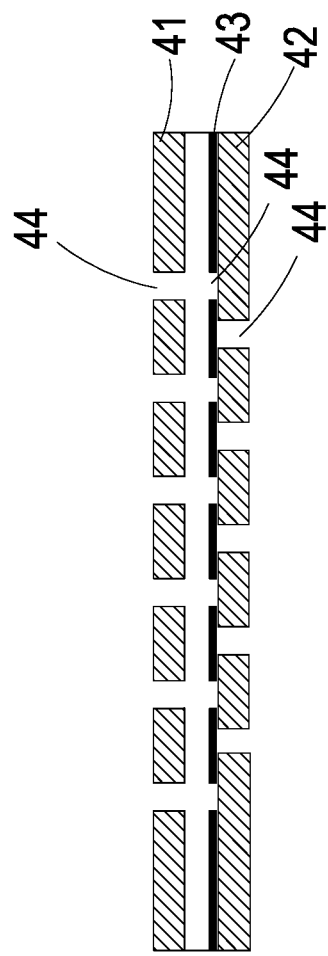
FIGS. 7A and 7B show the actuations of a switch valve of the blood glucose monitoring and controlling system of FIG. 1.

Please refer to FIGS. 3 and 7A. In this embodiment, the switching valve 4 of the liquid supplying chamber 23 of the liquid supplying device 2 includes a stationary component 41, a sealing component 42 and a displacement component 43. The displacement component 43 is disposed between the stationary component 41 and the sealing component 42. The stationary component 41, the sealing component 42 and the displacement component 43 have a plurality of orifices 44, respectively. The orifices 44 of the displacement component 43 are aligned with the orifices 44 of the stationary component 41. The orifices 44 of the sealing component 42 are misaligned with the orifices 44 of the stationary component 41.

Figure 7B:
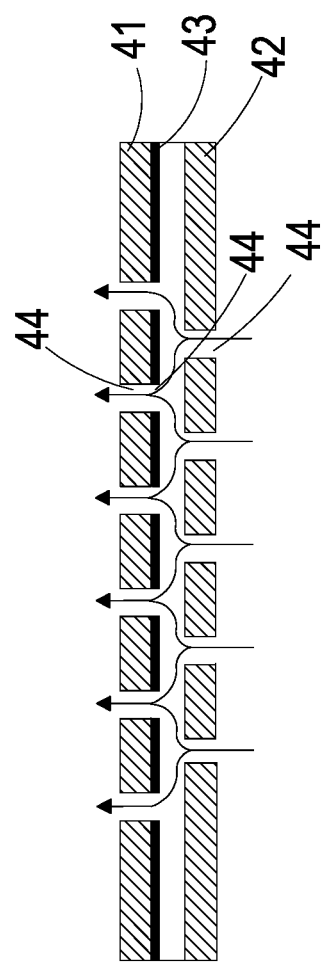

Please refer to FIG. 7A. In a first aspect of the switching valve 4 in the present disclosure, the displacement component 43 is made of a charged material, and the stationary component 41 is made of a bipolar conductive material. In case that the stationary component 41 and the displacement component 43 are maintained in the same polarity, the displacement component 43 moves toward the sealing component 42 to close the switching valve 4. Please refer to FIG. 7B. The displacement component 43 is made of a charged material, and the stationary component 41 is made of a bipolar conductive material. In case that the stationary component 41 and the displacement component 43 are maintained in opposite polarity, the displacement component 43 moves toward the stationary component 41 to open the switching valve 4. The polarity of the stationary component 41 is adjusted to cause the displacement component 43 to move so as to switch the open/closed states of the switch valve 4. The polarity of the stationary component 41 is controlled by the liquid supplying and controlling chip 24.

In a second aspect of the switching valve 4 in the present disclosure, the displacement component 43 is made of a magnetic material, and the stationary component 41 is made of an electromagnet material and can be controlled to change its magnetic polarity. In case that the stationary component 41 and the displacement component 43 are maintained in the same polarity, the displacement component 43 moves toward the sealing component 42 to close the switching valve 4. On the contrary, in case that the stationary component 41 and the displacement component 43 are maintained in opposite polarity, the displacement component 43 moves toward the stationary component 41 to open the switch valve 4. From the above descriptions, the polarity of the stationary component 41 is adjusted to cause the displacement component 43 to move so as to switch the open/closed states of the switch valve 4. The magnetic polarity of the stationary component 41 is controlled by the liquid supplying and controlling chip 24.

Please refer to FIG. 8. The transmitting module 141 and the receiving module 241 may be in signal communication with each other via a wired transmission technology or a wireless transmission technology. The wired transmission technology includes a wired transmission module. The wired transmission module is at least one selected from the group consisting of a USB port, a mini-USB port and a micro-USB port. The wireless transmission technology includes a wireless transmission module. The wireless transmission module is at least one selected from the group consisting of a Wifi module, a Bluetooth module, an RF module and a NFC module.

From the above descriptions, the present disclosure provides a blood glucose monitoring and controlling system. When the first microneedle patch of the detecting device is punctured into the subcutaneous tissue of the human subject, the liquid pumping actuator is actuated to generate the pressure gradient, so that the tissue liquid of the subcutaneous tissue is drawn by the suction force of the hollow microneedles of the first microneedle patch and transported to the liquid storage chamber owing to the actuation of the first actuating unit. The sensor within the liquid storage chamber measures and analyzes the blood glucose level in the tissue liquid, and transmits the measured data to the monitoring and controlling chip. When the blood glucose level of the user is abnormal, the monitoring and controlling chip transmits the blood glucose level information to the liquid supplying and controlling chip of the liquid supplying device for allowing the liquid supplying actuator to be rapidly actuated by the liquid supplying and controlling chip, so that the insulin liquid can be injected into the user's body in real time to maintain and stabilize the blood glucose level. The blood glucose monitoring and controlling system of the present disclosure is used to measure the blood glucose level easily and simply at anytime and anywhere so that the troubles of measuring the blood glucose by the user are addressed. When the blood glucose level is abnormal, the insulin liquid can be injected into the user's body rapidly so as to stabilize the blood glucose level constantly and thereby address the issues that the diabetes mellitus patients fail to stabilize the blood glucose level efficiently for a long period of time. In addition, the present disclosure utilizes the microneedle patch to use non-invasive or microinvasive technology to obtain the tissue liquid of the subcutaneous tissue for measuring the blood glucose level so as to reduce the burden of the user, avoid the generation of wounds and reduce the risk of infection.

While the disclosure has been described in terms of what is presently considered to be the most practical and preferred embodiments, it is to be understood that the disclosure needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A blood glucose monitoring and controlling system, comprising:
a detecting device comprising a first microneedle patch, a liquid pumping actuator, a sensor and a monitoring and controlling chip, wherein:
the first microneedle patch comprises a plurality of hollow microneedles configured to be attached to and punctured into skin of a human subject to draw a tissue liquid;
the liquid pumping actuator comprises a liquid guiding channel, a first actuating unit, a first carrier body, a first compressing chamber and a liquid storage chamber, the liquid guiding channel is in fluid communication with the first microneedle patch, and the first actuating unit is constructed on the first carrier body and covers and seals the first compressing chamber, the first microneedle patch is attached on the first carrier body and is opposite to the first actuating unit, and first actuating unit is actuated to generate a first pressure difference in the liquid guiding channel to draw the tissue liquid and allow the liquid guiding channel to draw the tissue liquid transported by the hollow microneedles, wherein the liquid guiding channel comprises an inlet channel and a liquid storage channel separately disposed in the first carrier body, the first compressing chamber is in fluid communication with the inlet channel and the liquid storage channel, and the liquid storage channel is in fluid communication with the liquid storage chamber, wherein a valve membrane is disposed in the inlet channel and the liquid storage channel to control an open/closed state of the inlet channel and the liquid storage channel;
the sensor is packaged in a system-in-package manner on the first carrier body and is disposed in the liquid storage chamber and is in communication with the liquid guiding channel to measure a blood glucose level in the tissue liquid and transmits a measured data of the blood glucose level to the monitoring and controlling chip; and the monitoring and controlling chip generates blood glucose level information by calculating the measured data and transmits a notification of the blood glucose level information; and a liquid supplying device comprising a second microneedle patch, a liquid supplying actuator, a liquid supplying chamber and a liquid supplying and controlling chip, wherein:

the second microneedle patch comprises a plurality of hollow microneedles configured to be attached to and punctured into the skin of the human subject;

the liquid supplying actuator comprises a liquid injection channel, a second actuating unit, a second carrier body and a second compressing chamber, the second actuating unit is constructed on the second carrier body and covers and seals the second compressing chamber, the second microneedle patch is attached on the second carrier body and is opposite to the second actuating unit, and the liquid injection channel is in fluid communication with the second microneedle patch and the liquid supplying chamber;

the liquid supplying chamber stores an insulin liquid, and the second actuating unit is actuated to compress the liquid injection channel to conduct liquid transportation; and the liquid supplying and controlling chip receives the notification of the blood glucose level information transmitted from the monitoring and controlling chip of the detecting device so as to actuate the second actuating unit of the liquid supplying device so that a second pressure difference is generated in the liquid injection channel to transport the insulin liquid stored in the liquid supplying chamber and guide the insulin liquid to the hollow microneedles, thereby injecting the insulin liquid into subcutaneous tissue of the human subject to stabilize the blood glucose level.

2. The blood glucose monitoring and controlling system according to claim 1, wherein the monitoring and controlling chip is packaged in a system-in-package manner on the first carrier body, and the monitoring and controlling chip controls an actuation of the first actuating unit of the liquid pumping actuator, receives the measured data from the sensor to generate the blood glucose level information by calculating the measured data and comprises a transmitting module for transmitting the notification of the blood glucose level information.

3. The blood glucose monitoring and controlling system according to claim 2, wherein the transmitting module is a wireless transmission module, wherein the wireless transmission module is at least one selected from the group consisting of a Wifi module, a Bluetooth module, an RF module and a NFC module.

4. The blood glucose monitoring and controlling system according to claim 1, wherein the first carrier body further comprises a convex structure in each of the inlet channel and the liquid storage channel, and the convex structure is configured to provide a pre-force when the valve membrane is abutting against the convex structure, thereby preventing the tissue fluid from flowing back.

5. The blood glucose monitoring and controlling system according to claim 1, wherein the liquid injection channel comprises an outlet channel and a liquid guiding channel separately disposed in the second carrier body, the second compressing chamber is in fluid communication with the outlet channel and the liquid guiding channel.

6. The blood glucose monitoring and controlling system according to claim 5, wherein a valve membrane is disposed in the outlet channel and the liquid guiding channel to control an open/closed state of the outlet channel and the liquid guiding channel.

7. The blood glucose monitoring and controlling system according to claim 6, wherein the second carrier body further comprises a convex structure in each of the outlet channel and the liquid guiding channel, and the convex structure is configured to provide a pre-force when the valve membrane is abutting against the convex structure, thereby preventing the insulin liquid from flowing back.

8. The blood glucose monitoring and controlling system according to claim 5, wherein the liquid supplying and controlling chip of the liquid supplying device is packaged in a system-in-package manner on the second carrier body and comprises a receiving module for receiving the notification of the blood glucose level information transmitted from the monitor and controlling chip of the detecting device so as to control an actuation of the second actuating unit of the liquid supplying device.

9. The blood glucose monitoring and controlling system according to claim 8, wherein the receiving module is a wireless transmission module, wherein the wireless transmission module is at least one selected from the group consisting of a Wifi module, a Bluetooth module, an RF module and a NFC module.

10. The blood glucose monitoring and controlling system according claim 1, wherein each of the plural hollow microneedles of the first microneedle patch and the second microneedle patch has an internal diameter ranging from 10 µm to 550 µm and a length ranging from 400 µm to 900 µm, wherein the plural hollow microneedles of the first microneedle patch are arranged in a first array, the plural hollow microneedles of the second microneedle patch are arranged in a second array, and any two adjacent ones of the plural hollow microneedles are spaced from each other a distance greater than 200 µm, wherein the plural hollow microneedles of the first microneedle patch and the second microneedle patch are made of silicon dioxide.

11. The blood glucose monitoring and controlling system according to claim 1, wherein the liquid supplying chamber has a liquid supplying outlet, and a switch valve is disposed in the liquid supplying outlet, wherein the switch valve comprises a stationary component, a sealing component and a displacement component, wherein the displacement component is disposed between the stationary component and the sealing component, and the stationary component, the displacement component and the sealing component each contain plural orifices, wherein the plural orifices of the stationary component are aligned with the plural orifices of the displacement component, and the plural orifices of the sealing component are misaligned with the plural orifices of the stationary component.

12. The blood glucose monitoring and controlling system according to claim 11, wherein the displacement component is made of a charged material, and the stationary component is made of a bipolar conductive material, wherein the displacement component and the stationary component are maintained in opposite polarity, and the displacement component moves toward the stationary component so that the switch valve is in the open state.

13. The blood glucose monitoring and controlling system according to claim 11, wherein the displacement component is made of a charged material, and the stationary component is made of a bipolar conductive material, wherein the displacement component and the stationary component are maintained in the same polarity, and the displacement component moves toward the sealing component so that the switch valve is in the closed state.

14. The blood glucose monitoring and controlling system according to claim 11, wherein the displacement component is made of a magnetic material, and the stationary component is made of an electromagnet material whose magnetic polarity is changeable under control, wherein the displacement component and the stationary component are maintained in opposite polarity, and the displacement component moves toward the stationary component so that the switch valve is in the open state.

15. The blood glucose monitoring and controlling system according to claim 11, wherein the displacement component is made of a magnetic material, and the stationary component is made of an electromagnet material whose magnetic polarity is changeable under control, wherein the displacement component and the stationary component are maintained in the same polarity, and the displacement component moves toward the sealing component so that the switch valve is in the closed state.

\* \* \* \* \*